US012746245B2

(12) United States Patent
O'Neil

(10) Patent No.: US 12,746,245 B2
(45) Date of Patent: Sep. 29, 2026

(54) TREATMENT OF INFLAMMATORY DISEASES OF THE CENTRAL NERVOUS SYSTEM

(71) Applicant: PALMAYA PTY LTD, Subiaco (AU)

(72) Inventor: Alexander George Brian O'Neil, Subiaco (AU)

(73) Assignee: Palmaya PTY LTD, Subiaco (AU)

( * ) Notice: Subject to any disclaimer, the term of this patent is extended or adjusted under 35 U.S.C. 154(b) by 1075 days.

(21) Appl. No.: 17/593,249

(22) PCT Filed: Mar. 16, 2020

(86) PCT No.: PCT/AU2020/050251

§ 371 (c)(1),
(2) Date: Sep. 14, 2021

(87) PCT Pub. No.: WO2020/181340

PCT Pub. Date: Sep. 17, 2020

(65) Prior Publication Data

US 2022/0152044 A1 May 19, 2022

(30) Foreign Application Priority Data

Mar. 14, 2019 (AU) ................................ 2019900851
Apr. 11, 2019 (AU) ................................ 2019901261

(51) Int. Cl.
*A61K 31/5517* (2006.01)
*A61K 9/00* (2006.01)
*A61K 31/485* (2006.01)

(52) U.S. Cl.
CPC ........ *A61K 31/5517* (2013.01); *A61K 9/0024* (2013.01); *A61K 31/485* (2013.01)

(58) Field of Classification Search
CPC .............. A61K 2300/00; A61K 31/485; A61K 31/5517; A61K 9/0024; A61P 25/04; A61P 25/06; A61P 25/16; A61P 25/28; A61P 25/32; A61P 25/30; A61P 25/36
See application file for complete search history.

(56) References Cited

U.S. PATENT DOCUMENTS

| | | | | |
|---|---|---|---|---|
| 2004/0241204 A1* | 12/2004 | Martinod | A61K 9/0024 | 424/426 |
| 2016/0089379 A1* | 3/2016 | O'Neil | A61P 25/16 | 514/220 |
| 2016/0213680 A1 | 7/2016 | Hassan et al. | | |

FOREIGN PATENT DOCUMENTS

| | | | |
|---|---|---|---|
| WO | 2009114740 | A9 | 9/2009 |
| WO | 2010094074 | A1 | 8/2010 |
| WO | 2012006683 | A1 | 1/2012 |
| WO | 2014186824 | A1 | 11/2014 |
| WO | 2015054730 | A1 | 4/2015 |

OTHER PUBLICATIONS

Durham et al., Neurological mechanisms of migraine: potential of the gap-junction modulator tonabersat in prevention of migraine, Cephalalgia, vol. 29 (Suppl 2), 1-9, Jul. 24, 2011 (Year: 2011).*
Pinkerton et al., Menstrual cycle-related exacerbation of disease, American Journal of Obstetrics and Gynecology, vol. 202, No. 3, 1-23, Jun. 3, 2011 (Year: 2011).*
International Application No. PCT/AU2020/050251, International Search Report and Written Opinion mailed May 21, 2020, 10 pages.
Kitamura, E., et al.; "Molecular and Cellular Neurobiology of Spreading Depolarization/Depression and Migraine; A Narrative Review", International Journal of Molecular Sciences, Oct. 17, 2024, vol. 25, 11163, 14 pages.
Bialer, M., et al.; "Progress Report on New Antiepileptic Drugs; A summary of the Eleventh Eilat Conference (EILAT XI)", Epilepsy Research, vol. 103, Dec. 4, 2012, 29 pages.
Silvestro, M., et al.; "Migraine Treatment: Towards New Pharmacological Targets", International Journal of Molecular Sciences, vol. 24, Jul. 31, 2023, 30 pages.
Roche Laboratories Inc., "Flumaznil", Package Insert, Feb. 2007, 18 pages.
Moskowitz, A.; "Rethinking migraine with aura; Why cortical spreading depolarization (depression), not aura, causes headaches", Cephalalgia, An International Journal of Headache, vol. 45, Aug. 5, 2025, 6 pages.

* cited by examiner

*Primary Examiner* — Sarah Pihonak
*Assistant Examiner* — Padmaja S Rao
(74) *Attorney, Agent, or Firm* — Leber IP Law; Celia H. Leber

(57) ABSTRACT

The present invention relates to the use of flumazenil for the treatment of inflammatory conditions of the central nervous system, such as migraine, headache and multiple sclerosis, anxiety, PTSD, psychosis, depression, and cessation of addictive behaviours. The active may be administered in the form of an implant. The present invention also relates to the use of flumazenil, naltrexone, and optionally buprenorphine in order to reduce symptoms associated with withdrawal of drugs of dependence or addictive behaviours.

10 Claims, 1 Drawing Sheet

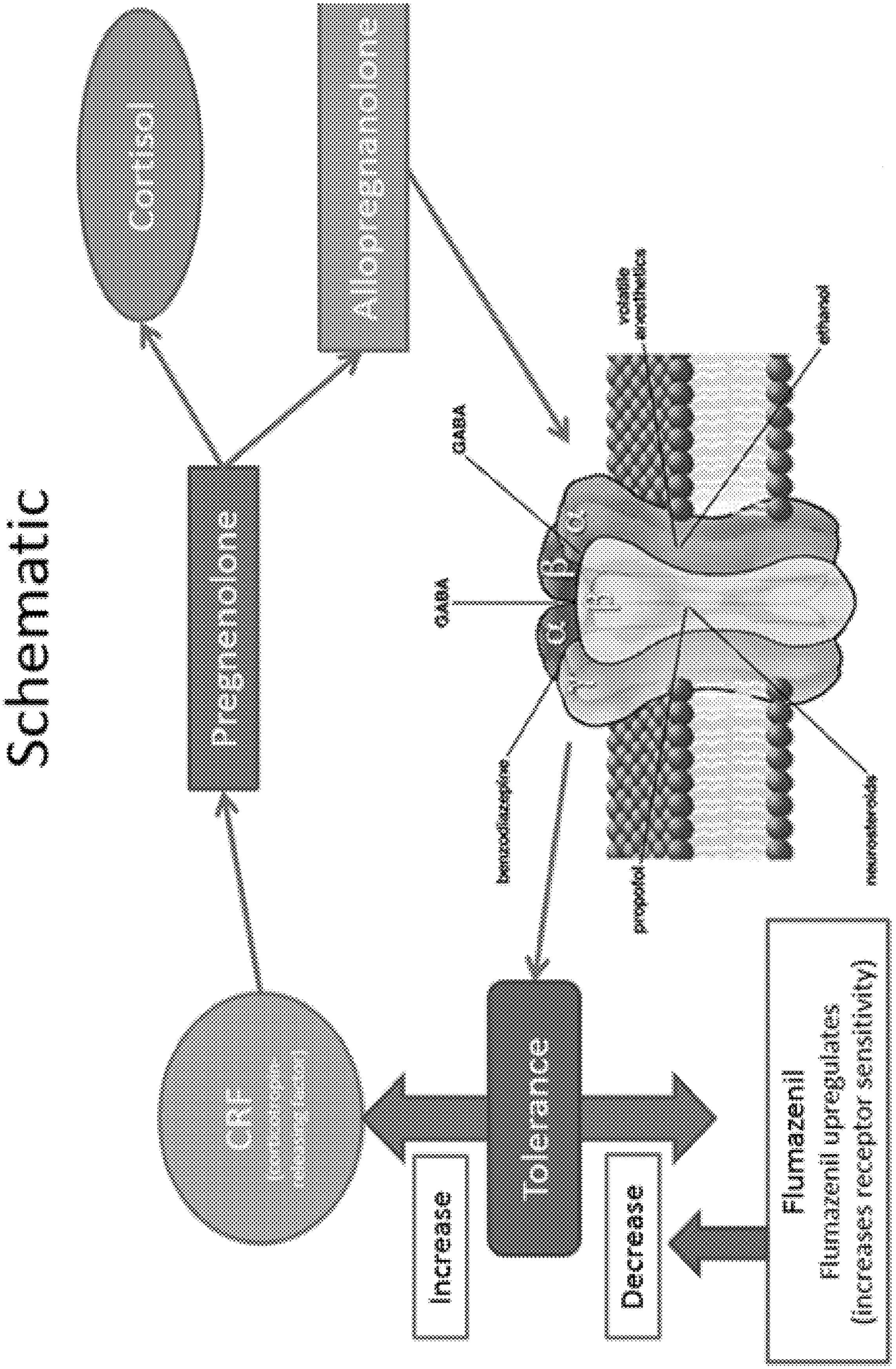
Schematic
Cortisol
Pregnenolone
Allopregnanolone
CRF
GABA
GABA
α
β
α
volatile anesthetics
ethanol
benzodiazepine
propofol
neurosteroids
Tolerance
Increase
Decrease
Flumazenil
Flumazenil upregulates
(increases receptor sensitivity)

TREATMENT OF INFLAMMATORY DISEASES OF THE CENTRAL NERVOUS SYSTEM

RELATED APPLICATIONS

This application is a national phase entry of International Patent Application No. PCT/AU2020/050251, filed Mar. 16, 2020, which claims priority from Australian patent application nos. 2019900851 and 2019901261 filed Mar. 14, 2019, and Apr. 11, 2019 respectively.

TECHNICAL FIELD

The present invention relates to compositions and methods for treating diseases, disorders or conditions associate with inflammation of the central nervous system, as well as symptoms associated with detoxification of patients using drugs.

BACKGROUND ART

The following discussion of the background art is intended to facilitate an understanding of the present invention only. The discussion is not an acknowledgement or admission that any of the material referred to is or was part of the common general knowledge as at the priority date of the application.

Gamma-aminobutyric acid (GABA) is believed to be the main inhibitory neurotransmitter in the brain, and acts on a variety of GABA receptors. There are a large number of different GABA receptors, including $GABA_A$ receptors ($GABA_AR$). In addition to the primary binding sites for GABA, the $GABA_AR$ has other secondary binding sites for molecules that modulate the effect of GABA, such as benzodiazepines, barbiturates, steroids, and alcohol.

The general understanding is that these modulating agents alter the efficiency of chloride ion transfer into the cell. This change modifies the size of the channel, which in turn modifies the receiving neuron's permeability to chloride ions. Since chloride ions are negatively charged, when they enter the neuron, they hyperpolarize the cell.

When GABA interacts with its receptor site, the result is a trickle of ions into the cell. However, when a benzodiazepine interacts with the GABA receptor, it amplifies the GABA effect of ions into the cell, resulting in hyperpolarisation of the cell, and cell damage or cell death.

Addiction to a variety of drugs has also been associated with the $GABA_AR$. Furthermore, migraines and multiple sclerosis may be considered to be related to the $GABA_AR$, and it is possible that other inflammatory diseases of the Central Nervous System (CNS) are associated with the $GABA_AR$.

Opioid dependence is an addiction to opioids, such as drugs used to treat pain or heroin. The opioids act on the opioid receptors and an individual may develop an addiction to the opioids. Craving for the opioid is associated with opioid dependence. In addition, substances, including alcohol and non-opiate drugs such as nicotine, alcohol, marijuana, benzodiazepines, amphetamines, and behaviours, including gambling all produce a feeling of pleasure through elevations of dopamine and opiates by the endogenous release of these substances. These effects may be reduced by the presence of an opioid antagonist or partial agonist having a blocking effect at the opioid receptor sites, and so reduces pleasure from the substance or behaviour and also reduces craving for the substance or behaviour.

An opioid antagonist is a molecule that interacts with the opioid receptor. Common opioid antagonist drugs include naloxone and naltrexone, which are termed "competitive antagonists" since they bind to the opioid receptors with high affinity than agonists and do not activate the receptors.

In contrast, an opioid partial agonist binds to the opioid receptor with less affinity that an opioid antagonist, thus acting as a competitive antagonist and will usually partially activate the receptor. Examples of partial antagonists include buprenorphine, nalmefene and norclozapine.

Naltrexone is a drug commonly used in oral form to assist in the detoxification or long term maintenance of opioid dependence, and also as a treatment for alcohol addiction. Naltrexone blocks the effects of opioids by blocking the opioid receptor. It is thought that if a person does not experience any positive effect on repeated exposure when using the opioid, that person usually will eventually cease opioid or alcohol use. The literature shows that naltrexone has a limited but useful place in treating addiction but by itself has a high failure rate with managing addiction outside opiates or alcohol.

As with all addictions, craving anxiety builds and is then reduced at the time of drug use or when the habit is repeated. The cycle then repeats itself. Craving may present itself with anxiety or in some cases presents itself where the individual places himself in a risky situation or searches for the substance or opportunity for the substance or event. With oral naltrexone the absorption from the stomach is slow (up to a hour with the added problem of liver breakdown of naltrexone) and so the time waiting for correction of craving following an oral dose of naltrexone is so long that the craving will have often driven the individual to use before the usual oral dose has had any effect on craving for alcohol, smoking or drug use.

Flumazenil is an antagonist at the benzodiazepine section of the GABA receptor. It has mainly been used commercially in the management of benzodiazepine overdose where it returns patients to consciousness and returns the respiratory drive back to normal. It has been available for 30 years and is only commercially used intravenously with a purpose to resuscitate benzodiazepine overdose patients. The literature describes the fact that intravenous flumazenil may block the benzodiazepine receptor sites and is associated with side effects such as panic attacks or fitting.

The literature on flumazenil suggests it may have a role in the treatment of a number of addictions. Clinically, however there is no well-established place for flumazenil in addiction management. Furthermore, there appears to be no significant literature on the use of flumazenil in the treatment of addiction to smoking cigarettes or marijuana.

Flumazenil is prepared for injection for intravenous use only, and is supplied as 5 ml or 10 ml, multi-use vials, containing 0.1 mg/ml flumazenil. Flumazenil may be prepared in 5% dextrose in water, lactated Ringer's and normal saline solutions.

Flumazenil is indicated for reversal of sedation, and benzodiazepine overdose in adults and pediatric use (1-17 years of age). For example, adult use for reversal of sedation requires an initial intravenous dose of 0.2 mg one time over 15 seconds, repeated every minute until the desired level of consciousness is achieved, to a maximum dose of 1 mg.

Buprenorphine is an opioid used to treat opioid addiction, acute pain and chronic pain. It is considered to be a mix of an opioid antagonist-agonist.

Migraine is a complex neurological condition that is characterised by severe, episodic attacks of headache and associated symptoms, such as nausea, vomiting, sensitivity to light, sound or movement. An aura may precede or coincide with the headache.

Migraines represent an inflammatory disease of the central nervous system with episodes that are episodic. Research suggests that women present with migraines three time more frequently than men (see Peterlin et al., (2011); "*Sex Matters: Evaluating Sex and Gender in Migraine and Headache Research*", Headache, 51(6): 839-842). Furthermore, research also suggests that multiple sclerosis occurs more often in women than men (see Harbo et al., (2013); "*Sex and Gender Issues in Multiple Sclerosis*"; Ther. Adv. Neurol. Disord. 6(4), 237-248).

Migraine and multiple sclerosis may be considered as inflammatory episodes which present in the late luteal phase of menstruation, typically lasting for about two days, and the first three days of the follicular phase (first three days of menstruation).

Premenstrual dysphoric disorder (PMDD) also occurs in the same phase of the menstrual cycle as multiple sclerosis and migraines. All three conditions are increased when progesterone and allopregnanolone levels drop (for example, post-menopausal, puerperium and premenstrual) and are reduced in incidence and severity when pregnanolone and progesterone are high, for example during pregnancy.

Interestingly, migraines occur about three times more often in multiple sclerosis patients. Multiple sclerosis occurs about three time more often in migraine patients. A link between multiple sclerosis, migraines and PMDD is becoming recognised.

Presently, there is no reliable or successful treatment of migraine, multiple sclerosis or other diseases, disorders or conditions associated with inflammation of the central nervous system. Furthermore, there exists a need to develop a method of treatment of symptoms associated with drug use, severe cravings, and/or stress which will cause rapid settling of the craving for substance use, and/or obsessional behaviour. It is against this background that the present invention has been developed.

SUMMARY OF INVENTION

The inventors have surprisingly found that the use of a continuous infusion of a low dose of flumazenil either alone or in combination with an opioid antagonist or partial-antagonist is effective in the treatment of inflammatory diseases associated with the central nervous system, including migraines and multiple sclerosis, and in particular, the treatment of migraines and headaches in women.

In one aspect of the present invention, there is provided an implant comprising: (i) an effective amount of flumazenil and (ii) a non-absorbable polymers, wherein the non-absorbable polymers release the flumazenil into the subcutaneous tissue of a patient in need thereof over a continuous period of time.

In one embodiment, the implant delivers a continuous dose of between about 60 to 80 micrograms of flumazenil per hour for a prolonged period of time. In a further embodiment, the flumazenil is maintained at a blood concentration in the patient of about 0.5 ng/ml during treatment.

In a further aspect of the present invention, there is provided a method of treating a patient suffering from an inflammatory disease of the CNS, comprising administering to the patient in need thereof an effective dose of flumazenil to achieve a blood concentration of flumazenil at about 0.5 ng/ml flumazenil over a continuous and prolonged period of time.

In a further aspect of the present invention, there is provided a method of treating a patient suffering from an inflammatory disease of the CNS comprising administering to the patient in need thereof an effective dose of flumazenil of between 60 to 80 micrograms flumazenil per hour for a continuous period of time. In one embodiment, the delivery is via subcutaneous infusion or subcutaneous implants.

In one embodiment, the method of the present invention is used in the treatment of migraine in a subject, comprising the steps of: administering a subcutaneous implant delivering about 60-80 micrograms per hour of flumazenil to obtain a blood level of about 0.5 ng/ml to 3.0 ng/ml flumazenil for a continuous period of time; and optionally administering a second subcutaneous implant delivering an estimated 60-80 micrograms per hour of flumazenil to obtain a blood level of about 0.5 ng/ml to 3.0 ng/ml flumazenil over a continuous period of time.

In one preferred embodiment, the implant releases flumazenil at an effective amount for between about 8-10 weeks. In a highly preferred embodiment, the implant prevents the occurrence of migraine or symptoms associated with migraine for about 9-10 weeks, or longer. In another embodiment, one or more implants may be administered to the patient on return of the migraine or associated symptoms.

In one embodiment, the method of the present invention is used in the treatment of migraine in a subject, comprising the steps of: administering an initial subcutaneous infusion of flumazenil at a rate of 160 micrograms per hour, over a continuous period of time to the subject; followed by the administration of a subcutaneous implant delivering about 60-80 micrograms per hour of flumazenil to obtain a blood level of about 0.5 ng/ml to 3.0 ng/ml flumazenil for a continuous period of time; and optionally administering a second subcutaneous implant delivering an estimated 60-80 micrograms per hour of flumazenil to obtain a blood level of about 0.5 ng/ml to 3.0 ng/ml flumazenil over a continuous period of time.

In one preferred embodiment, the implant releases flumazenil at an effective amount for about 8-10 weeks. In a highly preferred embodiment, the implant prevents the occurrence of migraine or symptoms associated with migraine for about 9-10 weeks, or longer. In another embodiment, one or more implants may be administered to the patient on return of the migraine or associated symptoms.

In another embodiment, the methods of the present invention as described above may be used in the treatment of multiple sclerosis.

In a further aspect, the present invention provides the use of flumazenil in the preparation of a medicament, wherein the medicament comprises a low dose of flumazenil in the treatment of an inflammatory disease of the CNS.

Furthermore, we have discovered that the combination of naltrexone and flumazenil is useful in the management of symptoms associated with detoxification of patients using single and poly drug use, and related stress. The continuous delivery of naltrexone and flumazenil at rates of 40-200 micrograms per hour, and maintaining a plasma concentration of approximately 0.5 ng/ml to 4 ng/ml or greater effect the $GABA_A$ system and the opioid system in a manner that reduces or eliminates some or most of the severe symptoms of drug craving, drug withdrawal and stress related symptoms.

Therefore, in one aspect of the present invention, there is provided a method of treating a patient in need thereof comprising administering an effective dose of naltrexone in combination with flumazenil.

In another aspect of the present invention, there is provided a method of treating a patient in need thereof comprising administering a continuous dose of naltrexone and flumazenil prior to the ceasing of drug use followed by a continuous dose of naltrexone and flumazenil to reduce symptoms associated with withdrawal of the drug.

In a further aspect of the present invention, there is provided a composition comprising naltrexone, flumazenil and buprenorphine when used in the management of single or poly drug use, wherein each of naltrexone, flumazenil and buprenorphine are administered at a rate of at least 40 μg/hour.

In a further aspect of the present invention, there is provided a method of treating withdrawal symptoms associated with single drug use or poly drug use, wherein flumazenil and buprenorphine are administered together for at least one day preceding the addition of naltrexone. In one embodiment, the naltrexone is administered on day 2 to day 4 after commencement of the flumazenil and buprenorphine.

In one embodiment of the present invention, there is provided a method of managing the symptoms associated with opioid withdrawal, wherein the method comprises infusions of flumazenil at a concentration of 160 μg/hour and buprenorphine at a rate of 20 or 40 μg/hour for 24 to 72 hours following withdrawal of the opioid, followed by a dose of naltrexone at least 100 μg/hour for a period of time required to observe a reduction in the symptoms associated with opioid withdrawal.

In a further aspect of the present invention, there is provided the long term delivery of naltrexone and flumazenil at rates at or above 40 μg/hour to control symptoms associated with addiction and stress. In one embodiment, the long term use of naltrexone and flumazenil at rates at or above 40 μg/hour controls or reduces the use of one or more drugs in drug dependent patients and/or stress related diseases or disorders including hypertension, diabetes, and cancer.

BRIEF DESCRIPTION OF DRAWINGS

FIG. 1 is a schematic diagram showing the dysregulation of the $GABA_A$ system with excessive $GABA_A$ receptors appears to predispose to hyperpolarisation, inflammation and potentially cell death.

DESCRIPTION OF EMBODIMENTS

General Description of the Invention

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg. size, displacement and field strength etc). A range of values will be understood to include all values within the range, including the values defining the range, and values adjacent to the range which lead to the same or substantially the same outcome as the values immediately adjacent to that value which defines the boundary to the range.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent, or may encompass two or more active agents.

The term "disorders", diseases", or "conditions" may be used interchangeably to define a disease, disorder or condition which effects the human body.

The term "effective amount" as applied to "one or more active agents" refers to that amount which is sufficient to effect the desired change in the subject. It is within the knowledge and skill of a person skilled in the art to determine the effective amount of an active agent.

By "biodegradable" is meant a material that should degrade by bodily processes to products readily disposable by the body and should not accumulate in the body. The products of the biodegradation should also be biocompatible with the body.

By "biocompatible" is meant not toxic to the human body, is pharmaceutically acceptable, is not carcinogenic, and does not significantly induce inflammation in body tissues.

The term "treatment" as used herein covers any treatment of a disease in an animal (including a human), and includes: (i) preventing the disease from occurring; (ii) inhibiting the disease, i.e., arresting its development; (iii) relieving the disease, i.e., causing regression of the disease; or (iv) modifying normal biological activity such as in the case of cravings, promotion of weight gain or contraception.

While the pharmaceutical preparations prepared herein may be administered in any form, preferably they are adapted for drug delivery beneath subcutaneous tissue, including subcutaneous infusion or subcutaneous implants. The pharmaceutical preparations may also be administered as a spray to the mucosal or oral membranes.

The term "implant(s)" refers to any object that may be required to be administered to a patient for a pharmaceutical effect including the pharmaceutical preparation of the present invention. For the purposes of this specification, the term 'implant(s)' refers to a pharmaceutical preparation comprising an active agent. In a preferred embodiment, the implant comprises at least flumazenil or an imidazobenzodiazepine derivative as the active agent.

The term "dependence" may apply to opioids, alcohol, smoking nicotine, marijuana, cocaine, amphetamines, other substances, obsessional behaviour characterised by gambling, temper tantrums, or episodes of terror or post-traumatic stress disorders.

The term "craving" is defined as an increasing desire or need that gradually controls the individual's behaviour until the desired substance or experience is achieved.

The term "active agent" may mean one active agent, or many encompassing two or more active agents.

The term "dependency" generally refers to a craving for, habituation to, or addiction to a chemical or other substance.

The term "inflammatory disease of the Central Nervous System (CNS)" includes diseases associated with neuro-inflammation. An inflammatory disease includes migraines, multiple sclerosis, neuromyelitis optica (NMO), transverse myelitis, optic neuritis, acute disseminated encephalomyelitis (ADEM), primary angiitis of the central nervous system, autoimmune limbic encephalitis, and Susac's syndrome, sarcoidosis, systemic lupus erythematosus (SLE), giant cell arteritis, Behçet's disease, Sjögren's, and other vasculitides.

The term "migraine" includes migraine with our without aura, hemiplegic migraine, cluster headaches, migrainous neuralgia, chronic headaches, tension headaches, and headaches resulting from other medical conditions, such as infection or increase pressure to the skull.

Throughout this specification, unless the context requires otherwise, the word "comprise" or variations such as "comprises" or "comprising", will be understood to imply the inclusion of a stated integer or group of integers but not the exclusion of any other integer or group of integers.

DETAILED DESCRIPTION OF THE INVENTION

Without wishing to be bound by theory, it is believed that the underlying condition of inflammatory diseases of the central nervous system appears to be associated with the dysregulation of the $GABA_A$ system. It is believed that the flumazenil preparation and method of administration in accordance with the present invention will remove excess $GABA_A$ receptors from neurons in order to treat the inflammatory disease (including migraines and multiple sclerosis), and in the treatment of addiction, as well as conditions associated with detoxification from single or poly drug use.

The dysregulation of the $GABA_A$ system with excessive $GABA_A$ receptors appears to predispose to hyperpolarisation, inflammation and potentially cell death, leading to neuronal death in, for example, multiple sclerosis and other CNS degenerative disorders, as shown in FIG. 1. For example, as tolerance at the receptor increases, diseases/disorders or conditions, such as anxiety, depression, psychosis, premenstrual depression, migraines and neurodegenerative diseases, increase. The inventor believes that receptor changes cause dysregulation of the HPA axis with changes to immunological responses.

It is considered that with the present demonstration of the clinical efficiency of flumazenil (for example in preventing inflammation of the central nervous system), when continuously delivered to a patient in need thereof, flumazenil can be used to prevent, control, reduce or delay neuronal cell death, and therefore prevent, treat, control, ameliorate, reduce the incidence of or delay the development and/or progression of, diseases, conditions or disorders associated with the dysregulation of the $GABA_A$ system, including central nervous system diseases, and may also play a role in preventing aging, increasing the length of life of individuals.

In addition, correction of addictions and stress or post-traumatic stress disorders which include behavioural addictions and drug dependencies has been shown by the inventor to be effectively managed by the constant delivery of opioid antagonists and benzodiazepine antagonists simultaneously so that the dysregulation of the opioid and $GABA_A$ systems is corrected by adjusting the sensitivity of opioid and $GABA_A$ receptors. This allows the correction of the HPA axis damages by stress and by addictive behaviours and by medications or illegal drugs as they impact the individual after drug withdrawal.

The most common multiple drug addictions (i.e. poly drug use) are made up of the following groups: (1) nicotine, cannabis and alcohol; (2) nicotine, cannabis, alcohol and amphetamines; (3) nicotine, cannabis, cocaine and alcohol; (4) nicotine, amphetamines, and opioids; (5) nicotine, cannabis, amphetamines, cocaine, benzodiazepines or GABA modulating drugs; (6) nicotine, cannabis, opioids and benzodiazepines; and (7) cannabis, amphetamines, opioids and benzodiazepines.

Each of these combinations and other possible combinations, may occur one drug at a time, or in concurrent use. The present invention aims to correct the damage to the opioid and $GABA_A$ systems by sustained delivery of flumazenil and opioid antagonists with patients who have had long term drug addiction and stress related damage to the opioid and $GABA_A$ systems.

Thus, in one embodiment, the present invention provides the use of a sustained therapeutically effective amount of naltrexone in combination with flumazenil for a period of time. In some cases the treatment may be administered for a period of one month to 12 months, and in more severe cases, for several years, or indefinitely. In our experience, a number of patients require sustained delivery of naltrexone and flumazenil, and possibly for up to 10 years or more. This correction of the opioid and $GABA_A$ systems with long term flumazenil delivery is believed by the inventor to correct the dysfunction in the opioid and $GABA_A$ systems of patients with long term stress and addictive disorders.

In addition, acute and chronic stress or recurring stress relating to memory of traumatic events or behavioural addictions damages the $GABA_A$ and opioid systems with elevation of CRF, cortisol, adrenalin, noradrenaline, endogenous opioids, and endogenous benzodiazepines, such as allopregnanolone acting as a neurosteroid with positive modulation at the $GABA_A$ receptor. These stress reactions and molecules when released have profound effects at the opioid and $GABA_A$ receptors, so that the number of receptors on neurons increases, tolerance increases and the organism or person starts to respond to higher and higher levels of endogenous or externally supplied opioids and benzodiazepine molecules (molecules with positive modulation of the $GABA_A$ receptor).

Thus, drugs and molecules that are effected by the new treatments of the present invention include nicotine, alcohol, cannabis, amphetamines, cocaine, benzodiazepines, and opioids.

Our experiments with patients with exposure to stress, addictive behaviours, and with exposure to the above mentioned drugs and molecules, have defined those who are exposed to stress, addictive behaviours and those exposed to one or more drugs or medications as those having a common illness affecting stress response which is manifested by dysregulation of the opioid and $GABA_A$ systems.

Detoxifying from opiates (as well as other addictive agents) is often associated with unpleasant symptoms including insomnia, restlessness, pain, fatigue and diarrhoea. If a patient detoxifies without medication, the process and its symptoms may often last for 3 to 14 days, or even longer, depending on the amount and type of opiate the person has been using. Our studies have shown that the withdrawal from opioid dependence may be achieved using small doses of active agents, including flumazenil either alone or in combination with naltrexone. After detoxification, patients may also be prescribed additional medication to control cravings.

In one embodiment, we have found that a solution of flumazenil at 16 mg per 30 ml with a pH of 4±1 as a subcutaneous infusion at 40 to 160 μg per hour as our standard treatment reduces symptoms associated with benzodiazepine detoxification. During the first 24-48 hours we did not ask the patient to cease their benzodiazepine usage. Therefore, flumazenil may be used during benzodiazepine usage.

Furthermore, we noted a reduction in symptoms associated with drug or alcohol withdrawal, and the symptoms associated with cravings, when the patient received flumazenil either alone or in combination with naltrexone simultaneously at the doses discussed herein, and particularly, when naltrexone provided levels of 0.5 to 20 ng per ml naltrexone in the blood.

The use of flumazenil at 160 μg per hour (and between 40-1000 μg per hour) and naltrexone as a constant delivery (sustained release naltrexone) controls symptoms in detoxification, and helps prevent, the use of smoking, cannabis, alcohol, amphetamines, opioids, benzodiazepines, other drugs and behavioural addictions. It is thought that it is the use of both agents together, administered by sustained delivery that maximises control over these addictions.

We have further noted that in patients with a history of psychosis following cassation of cannabis, amphetamines and alcohol that the use of flumazenil alone, or flumazenil and naltrexone, by sustained delivery methods prevents the onset of psychosis in those with a history of psychosis with each detoxification. This reduction in anxiety and paranoid symptoms as well as florid psychosis is so profound that there is a strong basis for using flumazenil in those presenting with extreme anxiety, paranoid thoughts, as well as psychosis from non-drug induced psychosis. We have therefore extended our treatment to help minimise psychotic symptoms in non-drug affected patients.

We also believe that naltrexone and flumazenil help return the HPA axis (the interaction between the hypothalamus, pituitary gland, and adrenal glands, which plays an important role in the stress response) to normal in stressed animals in our studies. Neuro-inflammatory diseases, such as Alzheimer's, Parkinson's Disease and Multiple Sclerosis, are all increased by stress and we have found that naltrexone and flumazenil together decrease stress and inflammatory diseases. For this reason the combination of sustained release naltrexone and sustained release flumazenil using injections, implants or infusions would be expected to limit neuro-inflammatory diseases and their symptoms In summary, the results of our experiments are that the known use of opioid and benzodiazepine agonists tend to prolong the addiction and while they may give some control of symptoms, they do not correct the HPA axis on a long term basis or the recurring stress responses and addiction. We have discovered that the administration of opioid antagonists and benzodiazepine antagonists in low doses (as low as 40 μg/hour) act to correct the responses from these diseases when these low doses are used for long periods of time. Our experiments have concentrated on poly-drug addictions and on patients with behavioural addictions and those with damaged stress responses. Examples of the groups of addictions where we have used these treatments are described below.

Nicotine

Our studies showed that naltrexone reduced craving for nicotine with a reduction in craving and a reduction in use in most patients studied. Flumazenil also reduced craving and use when given by infusion or on a craving control basis when delivered nasally or sublingually with 50 to 200 micrograms per dose of flumazenil.

Alcohol

We have observed that patients treated with naltrexone at doses of 2 ng/ml (considered a therapeutic dose) return to drinking alcohol. We have observed that in this group of patients complain of increased irritability, increased anxiety, increased sleep disturbance, and/or increased aggressive behaviour. However, when administered together with flumazenil at a concentration of 40 to 160 μg/hour, these systems are controlled. Furthermore, patients have been shown to be less likely to return to alcohol use.

For patients with a history of relapse on naltrexone implants, the use of sustained release flumazenil with infusions initially and with a series of sustained release flumazenil implants delivering 40-160 μg/hour to sustain a concentration of 0.5 ng/ml or more appear to be useful in controlling the return to alcohol use. For example, we have shown that in women with a history of irritability and return to drinking in the premenstrual days, this treatment with sustained release flumazenil in combination with naltrexone, reduces craving and relapse patterns.

Cannabis

Cannabis use has changed in recent years with a significant cohort describing high tetrahydrocannabinol (THC) concentrations in potent strains which are cultivated for their high THC content. In the patient group using these high concentrations of THC, we have noted that a group of patients give a clear cut history of extreme nausea, vomiting, anxiety changing to serious paranoid thoughts and delusions followed by psychosis over the first 3-5 days of ceasing drug use.

In the group describing these symptoms, we have noted that flumazenil administered at a dose of 160 μg/hour delivers plasma concentrations of 0.5 ng/ml to 2 ng/ml, and controls or reduces the presence of these symptoms. In a severe patient population, ondansetron may be given every 6-8 hours to assist in reducing the nausea and associated anxiety symptoms.

Our results indicated a clear reduction in anxiety, and paranoid symptoms, allowing patients who otherwise would be unable to cope with the symptoms, to cease cannabis use. The use of naltrexone implants in these patients to achieve a plasma concentration of naltrexone from 0.5 ng/ml to 10 ng/ml or more reduces the craving and improves impulse control so that most patients can complete their cannabis detox with greatly reduced symptoms.

In the coming weeks after ceasing cannabis the patients who have a return to anxiety have a high risk of return to cannabis use. The use of flumazenil infusions and implants allows these patients to avoid return to cannabis use.

Amphetamines

In our observations with naltrexone implants, we have noticed a significant reduction in craving for amphetamine use if the plasma concentration of naltrexone are maintained at 2 ng/ml or higher. In our observations with methamphetamine patients, we have seen that those with a history of server withdrawal with symptoms that include psychosis or extreme anxiety, that flumazenil infusions at 160 μg/hour prevent these symptoms. In those patients that return 2-3 weeks with extreme anxiety and a desire to return to amphetamine use, the commencement of flumazenil infusions followed by a flumazenil implant that sustains a plasma concentration of flumazenil at 0.5-2 ng/ml or more decreases the cravings, including a decrease in the desire for amphetamines and allows reduction f irritability and aggression.

By delivering a series of implants every 2-4 months to sustain the flumazenil concentration in the blood, the withdrawal symptoms in these patients settled. We believe that many patients would not have been able to stop their drug use without the flumazenil treatment.

In high risk patients, the provision of a continuous delivery of naltrexone and flumazenil prior to ceasing their amphetamine use greatly reduces cravings and withdrawal symptoms. In our experience, we have used subcutaneous infusions and subcutaneous implants to achieve plasma concentrations between 0.5 and 4 ng/ml or higher with naltrexone and flumazenil to control or at least minimize the return to drug use and drug dependence.

Cocaine

Approximately 15 amphetamine patients have presented specifically for the control of their cocaine use using naltrexone implants. Approximately a third of these patients were from the United Kingdom, a third from Sydney, Australia and a third from Perth, Australia. This group of patients reported a reduction in craving with naltrexone implants, and most reported a reduction in cravings for 6-12 months after receiving the implant. Approximately half returned for repeat implants based on their observations that the naltrexone implant controlled their cravings. While we do not have experience with flumazenil with cocaine patients, our experience with methamphetamine patients suggests that the $GABA_A$ system is disturbed with stimulants and that flumazenil may be a useful medication for cocaine patients with symptoms of sleep, anxiety, and psychosis disorders.

Stress and Addictive Behaviours

Indigenous populations in for example, Australia, New Zealand, and the United States appear to be at risk of stress related diseases and particularly those of addictions. We believe these illnesses are a result of the $GABA_A$ system and the opioid system. These stress related illnesses include hypertension, diabetes, cancers and addictive disorders. Our observations with an estimated 15% of our patients being indigenous, are that naltrexone and flumazenil (both antagonists of the opioid and $GABA_A$ receptors) may be more effective or have a higher effect in indigenous patient populations. The use of these two antagonists together to prevent or manage stress related disorders such as hypertension, diabetes, premenstrual stress, multiple sclerosis, and cancers in indigenous populations, as well as other populations is strongly suggested by our research.

Benzodiazepines

Benzodiazepines bring relief to stress and are involved in the release of dopamine. As with all other significant addictions, self-control is extremely damaged in patients with a severe benzodiazepine addiction. Our observations of the treatment of poly-drug dependency which includes benzodiazepine usually responds well to the use of flumazenil at 40-160 μg/hour together with 40-160 μg/hour or greater. At this rate, positive modulation of the $GABA_A$ receptor with benzodiazepines is not significantly blocked by the presence of flumazenil. The continual delivery of flumazenil at this rate allows most patients to reduce their benzodiazepine dosing over a few days to a week or two. The control of symptoms as these patients cease their benzodiazepine is controlled so that the majority of patients can cease benzodiazepine use successfully.

Opioid Use

In the management of opioid withdrawal, flumazenil infusions delivered at 160 μg/hour and buprenorphine delivered at a rate of 20 or 40 μg/hour for 24-72 hours allows for withdrawal from opioids to be conducted with minimal symptoms. The use of naltrexone then at 100 μg/hour or more allows for a detox to occur with symptoms that are much reduced compared to earlier detox methods.

In opioid patients with long-standing addictions the continued delivery of flumazenil at 40 to 160 μg/hour or more with infusions and implants allows readjustment during the first 6 weeks to be much easier with better sleep and control of anxiety.

The present invention provides a method of managing the symptoms associated with opioid withdrawal, wherein the method comprises infusions of flumazenil at a concentration of 160 μg/hour and buprenorphine at a rate of 20 or 40 μg/hour for 24 to 72 hours following withdrawal of the opioid, followed by a dose of naltrexone at least 100 μg/hour for a period of time required to observe a reduction in the symptoms associated with opioid withdrawal.

Example—Cannabis Withdrawal

A 26 year old male described an estimated 20 or more hospital admissions during previos attempts to cease cannabis use. He describe commencing his cannabis use at the age of 11 years. His use started early as other members of this family were using cannabis, and he and his family were involved in cannabis cultivation.

He reported having stopped using cannabis for weeks at a time until the age of 16 years. From that time onwards, he had been unsuccessful in ceasing cannabis use and the twenty hospitalization episodes all related to extreme agitation, and a formal diagnosis of psychosis during the ten years from age 16 to age 26.

He described symptoms of withdrawal on day one after stopping cannabis use typically involving extreme nausea, often with vomiting, which were relieved with the use of cannabis. Day 2 post-ceasing cannabis use was associated with continued nausea and/or vomiting, and typically on day 2, anxiety that was uncontrolled, and considered the worst symptom. His usual use was 3 grams a day of a hydroponic variety with a reputation of being 27% THC. The cannabis was usually smoked mixed with nicotine.

Day 3 post-ceasing cannabis use was typically more severe than day 2 with severe paranoia and often suicidal thoughts.

From day 4 onwards, the symptoms usually required hospitalization for psychosis. Most hospitalization were short stays with resolution of the psychosis typically achieved within a day or and on the recommendations that cannabis use should be recommenced.

This patient was managed with a naltrexone implant releasing approximately 10 mg a day of naltrexone from day 2-3 and a flumazenil infusion of 160 μg/hour subcutaneously for the next 14 days. At the end of 14 days, the infusion was replaced with a flumazenil subcutaneous implant releasing approximately 80 μg/hour.

Eight weeks following the commencement of the above treatment, the patient described that, with exception of nausea (managed with sublingual ondansetron) in the first few days after ceasing cannabis use, he had no other medication. He experienced none of the anxiety, paranoid thoughts or psychotic symptoms that occurred consistent with all of his previous attempts to cease cannabis use.

Therefore, we conclude that the reduction in cravings is due to the combination of naltrexone and flumazenil. This is a completely new and surprising observation in the treatment of withdrawal from cannabis use, and in particular the use of cannabis with a high THC concentration

EXAMPLES

During our development of flumazenil ampoules we found that the preferred pH of the solution is approximately 4±1. The volume and dilution of the flumazenil solution was adjusted to 16 mg per 30 ml.

Flumazenil may be made up in any one of 5% dextrose in water, lactated Ringer's and normal saline solutions. Preferably, the flumazenil solution of the present invention is made up in any of the above solutions, and the pH adjusted to 4±1.

In our experience, this is the first flumazenil solution prepared for subcutaneous delivery making it possible to deliver 4 mg of flumazenil in a volume of just 7.5 ml per day. Clinically, this is preferred to the standard flumazenil preparations, which involve injecting 4 mg in 40 ml per day. For example, the lower volume results in less swelling at the site of injection.

Flumazenil may be delivered to a subject in need thereof by subcutaneous infusion. For example, a solution of flumazenil may be administered at a rate of 40 to 160 μg per hour to reduce systems associated with benzodiazepine detoxification or to treat migraines, symptoms of migraines or multiple sclerosis.

Flumazenil and Naltrexone Implants

The present invention provides for the delivery of a long acting active agent, for example flumazenil, together with a stable non absorbable polymer. The implant allows from about 60 mg to 80 mg per hour of flumazenil or naltrexone to be delivered subcutaneously over a prolonged period of time, including 4 weeks, 6 weeks, 8 weeks, 10 weeks or more.

In one example, the implant comprises a non-absorbable polymeric material and sufficient flumazenil (or naltrexone), for delivery of the active agent over 4 weeks up to 10 weeks or more. To control the release rate of the flumazenil, a 50:50 mixture of the polymeric material is made and then a film of the same polymeric material is applied which limits the release to the desired rate per day.

The implants of the present invention may be prepared by methods known to those skilled in the art.

Preparation of an Implant of Flumazenil or Naltrexone

The implants of the present invention are adapted to deliver the active agent at a constant rate for an extended (prolonged) period of time. Where the active agent is flumazenil, the rate of delivery is preferably about 10 to 300 micrograms per hour. The release rate may also be between 300 to 500 micrograms per hour, or 500 to 1000 micrograms per hour. The release rate may be up to 20,000 micrograms per hour. In some preferred embodiments, the release rate of flumazenil is between 40 to 300 micrograms per hour, between 50 to 250 micrograms per hour, between 60 to 200 micrograms per hour, between 80 to 150 micrograms per hour, or between 60 to 80 micrograms per hour.

The implants of the present invention release flumazenil over a prolonged period of time. For example, the prolonged period of time is 1 week, 2 weeks, 3 weeks, 4 weeks, 5, weeks, 6 weeks, 7 weeks, 8 weeks, 9 weeks, 10 weeks, 11 weeks, 12 weeks, 13 weeks, 14 weeks, 15 weeks, 16 weeks or more.

The amount of additional layers of the non-absorbable polymer material added to the outside of the implant will assist in controlling the release rate of the flumazenil from the implant. For longer lasting implants more layers of the polymer material may be added.

The implants of the present invention are adapted to deliver the active agent at a constant rate for an extended (prolonged) period of time. Where the active agent is naltrexone, the rate of delivery is preferably about 10 to 300 micrograms per hour. The release rate may also be between 300 to 500 micrograms per hour, or 500 to 1000 micrograms per hour. The release rate may be up to 20,000 micrograms per hour. In some preferred embodiments, the release rate of flumazenil is between 40 to 300 micrograms per hour, between 50 to 250 micrograms per hour, between 60 to 200 micrograms per hour, between 80 to 150 micrograms per hour, or between 60 to 80 micrograms per hour.

The implants of the present invention release naltrexone over a prolonged period of time. For example, the prolonged period of time is 1 week, 2 weeks, 3 weeks, 4 weeks, 5, weeks, 6 weeks, 7 weeks, 8 weeks, 9 weeks, 10 weeks, 11 weeks, 12 weeks, 13 weeks, 14 weeks, 15 weeks, 16 weeks or more.

The amount of additional layers of the non-absorbable polymer material added to the outside of the implant will assist in controlling the release rate of the naltrexone from the implant. For longer lasting implants more layers of the polymer material may be added.

Use of Flumazenil in the Treatment of Migraine

A 37 year old woman had a history of experiencing severe migraine, commencing just before her first menstrual period at the age of 12 years, which continued until the age of 37 years. The patient recently presented to our clinic, and was treated with flumazenil given subcutaneously at a rate of 160 micrograms per hour, delivered by a spring driven pump for a continuous period of time. The time that the migraines regularly occurred was the week prior to menstruation. However, the patient returned to the clinic when the migraine did not occur at the expected time.

The patient was then treated with a subcutaneous implant delivering an estimated 60-80 micrograms per hour of flumazenil (based on water bath release rate testing). The implant was expected to last 8-10 weeks. This prevented the migraines for about 9-10 weeks. In the week before the implant was inserted, the patient's blood flumazenil level was noted to be 0.5 ng/ml. The usual expected level for 160 microgram an hour infusions was in the order of 2-3 ng per ml and 1-1.5 ng for 80 microgram per hour infusions.

This finding that the migraines were stopped for a nine week period of time was amazing to the patient as she had suffered migraines for typically three weeks out of four for all of the years between the age of 12 and 37. At the end of week 8 on the first implant her blood flumazenil level was recorded as 0.5 ng per ml, which is considered a low level. Within a week another migraine started and the patient presented to the clinic for treatment.

A further subcutaneous implant was inserted and within four hours all symptoms from the migraine had settled. This was most unusual and unexpected as the symptoms following migraines usually persisted many days for this patient.

This next implant was also delivering an estimated 60-80 micrograms of flumazenil per hour. Evidence of ovulation was confirmed by routine elevation of progesterone during the luteal phase of one of the two cycles during the time of this second implant. Again no migraines occurred during an 8-9 week time of the second implant. Blood levels of flumazenil at 1.2 and 1.3 ng/ml were recorded during the time of the second implant. After 9-10 weeks the patient, presented to a teaching hospital on the weekend with another migraine. She was treated with all the modern treatments for migraines without resolution of the migraine.

A few days later a third implant was inserted. It again was surprising that all symptoms relating to the migraine settled within four hours.

Discussion of Studies Conducted with the Use of Flumazenil Alone or in Combination with Naltrexone in the Treatment of Symptom Associated with Detoxification, and Other Diseases, Conditions and Disorders Associated with an Inflammatory Response During our development of flumazenil ampoules we have found the preferred pH is about 4±1. In addition, the volume and dilution of flumazenil is preferably 16 mg per 30 ml. In our experience this was the first flumazenil made for subcutaneous delivery, and therefore, a dose of flumazenil at 4 mg can be administered in a volume of only 7.5 ml a day. Clinically, this is more convenient than the standard flumazenil ampoules which involve injecting 4 mg in a volume of 40 ml. Thus, a lower volume of the same amount of flumazenil resulted in less swelling of the tissues at the site of injection. In addition, the packaging of a dose of flumazenil of 16 mg in 30 ml enables clinical staff to use one ampoule for 4 days at 4 mg a day and one ampoule for 8 days at doses of 2 mg per day.

The same concentration of solution also provided a dose of just over 100 mcg (μg) per dose when used for nasal or sublingual delivery. In general, symptom relief demonstrated with subcutaneous infusions also occurred with subcutaneous flumazenil implants releasing similar delivery rates between 10 and 1000 mcg (μg) per hour.

We are also investigating the use of flumazenil and naltrexone via transdermal delivery. For example, we have used transdermal cream and flumazenil sprays to deliver flumazenil to decrease anxiety. Both these methods are excellent for sustained and bolus delivery of at least flumazenil.

Detoxification

Detoxifying from opiates (as well as other addictive agents) is often associated with unpleasant symptoms including insomnia, restlessness, pain, fatigue and diarrhoea. If a patient detoxifies without medication, the process and its symptoms may often last for 3 to 14 days, or even longer, depending on the amount and type of opiate the person has been using. Our studies have shown that the withdrawal from opioid dependence may be achieved using small doses of active agents. After detoxification, patients may also be prescribed additional medication to control cravings.

Our studies utilised either subcutaneous delivery or bolus dosing of flumazenil. Below is an example of the patients treated with flumazenil to treat addiction to opioids (e.g. benzodiazepines) or other addictive agents.

Reduction of Symptoms with Detoxing Off Benzodiazepines

We have used our solution of flumazenil at 16 mg per 30 ml with a pH of 4±1 as a subcutaneous infusion at 40 to 160 μg per hour as our standard treatment to reduce the symptoms associated with benzodiazepine detoxification. During the first 24-48 hours we did not ask the patient to cease their benzodiazepine usage.

Anticonvulsants, such as sodium valproate at 500 to 1000 mg per day were used for the first 10 days of flumazenil treatment to reduce the risk of epileptic seizures. Patients usually noted a decrease in their craving for benzodiazepines, and went on to cease benzodiazepine use within a few days to a week following commencement of the flumazenil infusion. The infusion may require several weeks of treatment and can be followed up with a flumazenil infusion delivering 40 to 160 μg per hour or more, as required to complete detoxification from the opioid.

Reduction of Symptoms Associated with Detoxification from Cigarettes

We have found a reduction in smoking of nicotine cigarettes with the use of flumazenil. We were able to document that those smoking changed from 82.7% before treatment to 75% following treatment in a group of 80 patients being treated with flumazenil. As well the increase in abstinence rates those using daily fell by 4% from 78.1% to 71.4% in the same population who had been treated with flumazenil.

Reduction of Symptoms Associated with Detoxification from Alcohol or the Use of Alcohol In a survey of 84 alcohol patients the percent of patients drinking daily fell from 14.5% to 5.5% following flumazenil infusions or implants. The percentage who were abstinent to alcohol increased from 53.1% to 77.1% following flumazenil treatment.

Reduction in Symptoms Associated with Detoxification from Cannabis

In a survey of 109 patients daily use was close to halved from 10% to 5.5%. Abstinence was increased from 75% to 83.5% in patients receiving a flumazenil infusion of the present invention. Patients who specifically presented to cease cannabis reported that nausea was decreased on day one, anxiety was decreased and sleep was better with the flumazenil infusion. Paranoid thoughts and psychotic thinking was reduced and suicidal thoughts were also reduced.

Reduction in Symptoms Associated with Detoxification from Amphetamines and Methamphetamine; and Reduction in Use In a survey of 109 patients treated with flumazenil 4.9% were using methamphetamines daily and this fell to 0.9% following treatment with the flumazenil infusion. Abstinence from methamphetamine use increased from 67% before flumazenil treatment to 87% following treatment. This means that 33% of patients using methamphetamines fell to 13% following treatment with flumazenil.

Reduction in Symptoms Associated with Detoxification from Opioids; and Use of Opioids In the 108 patients treated with flumazenil abstinence from opioids increased from 91.2% before flumazenil to 100% following the flumazenil treatment.

Reduction in Symptoms Associated with Detoxification from Any Dependency

In our 108 patents followed, there was a reduction in daily use of alcohol, smoking, cannabis, amphetamines, opioids and other drug use. In addition patients reported a reduction in anxiety and behavioural addictions.

Treatment of Other Diseases, Disorders and Conditions with Flumazenil Infusions or Implants Our studies over a number of years have collected data on the treatment of diseases, conditions or disorders in patients who presented to our clinic. Below is a summary of our observations.

Reduction in Anxiety without Cognitive Loss any Anxiety Situation

Twenty one patients were monitored after treatment with flumazenil for the following states: (i) calmness, (ii) tenseness, (iii) relaxation, (iv) contentedness, (v) worry; and (vi) upset.

In the population studied, all of these states improved, indicating a decrease in anxiety after treatment. A statically significant increase was noted in the levels of relaxation following treatment.

Reduction in Premenstrual Anxiety and Other Premenstrual Symptoms

We noted that women complaining of premenstrual tension specifically noted a reduction in premenstrual symptoms and a reduction in drug use and medication use.

Reduction in Anxiety Before and After Medication Delivery

We noted that patients had a reduction of anxiety during the time of medication delivery but also noted for many patients that their anxiety continued to be reduced for very long periods of time following flumazenil infusions. These observations appeared to indicate a cure or recovery of the patients underlying disease rather than relief of symptoms only. These observations included patients treated in five other years as well as the group treated in 2016-2017.

Reduction or Elimination of Migraines During and after Medication Delivery

Two migraine patients initially described migraine symptoms, are both symptom free for more than a year. No repeat treatments occurred in the second of the migraine patients, and as such, believe that the treatment might be curative in some patients.

In these two patients treated for migraines, the first patient the history of migraines affecting her required an infusion initially, and then flumazenil implants maintaining at least 1 ng per ml of flumazenil to achieve relief of symptoms. In a second patient we noted that the symptom relief has lasted for more than 12 months when treatment with a flumazenil implant lasting an estimated six months occurred. This data suggests that use of flumazenil may have resolved the underlying illness causing the illness of recurrent migraines in the second patient.

Reduction or Elimination of PTSD Symptoms with Flumazenil Alone

Post Trauma Stress Disorder (PTSD), causes dysregulation of anxiety control that may damage the $GABA_A$ system and present as hypervigilance, sleep disturbance, anxiety, gastrointestinal (GIT) or bladder symptoms. We have been using flumazenil for more than 8 years to treat patients presenting complex. The infusions and implants give relief to the anxiety, sleep disturbance and the GIT symptoms as well as urinary symptoms in many well established PTSD patients.

Reduction or Elimination of PTSD with Flumazenil and Naltrexone in Combination

We have noted significant improvement of PTSD symptoms with flumazenil alone and also in combination with naltrexone. We have noted that a severe case of waking at 2 am with shouting and anxiety which had occurred for 6 years stopped immediately as soon as a naltrexone implant was inserted. Sleep remained normal following this. The profound recovery of sleep in patients with PTSD using flumazenil and naltrexone by continuous delivery has not previously been described.

Reduction of Symptoms Associated with Drug or Alcohol Withdrawal and Craving Symptoms We noted a reduction in symptoms associated with drug or alcohol withdrawal, and the symptoms associated with cravings, when the patient received flumazenil and naltrexone simultaneously at the doses prescribed, and where naltrexone provides 0.5 to 20 ng per ml levels in the blood.

The use of flumazenil at 160 μg per hour (and between 40-1000 μg per hour) and naltrexone as a constant delivery (sustained release naltrexone) controls symptoms in detoxification, and helps prevent, the use of smoking, cannabis, alcohol, amphetamines, opioids, benzodiazepines, other drugs and behavioural addictions. It is thought that it is the use of both agents together, administered by sustained delivery that maximises control over these addictions.

Delivery of Flumazenil to Control Multiple Sclerosis

We have noted the close relationship between patterns of migraines in women and patterns of multiple sclerosis in women. Both have increased in the last 50 years and the incidence in migraines and multiple sclerosis are now both occurring three times more often in women compared to men.

Both these patterns have increased at similar rates in the 50 year period. Both appear to occur due to pathology in the benzodiazepine receptor with glial cells having a peripheral benzodiazepine receptor pathology and while migraines may be affected by the central and peripheral benzodiazepine receptors. Although not bound by theory, it is thought that both occur when allopregnenalone levels drop in the luteal phase of the mensural cycle. Our discovery that flumazenil causes recovery from migraines implies that this treatment and its effects on the $GABBA_A$ receptor might also help resolve the underlying disease causing multiple sclerosis. This link between the $GABA_A$ receptor, flumazenil and migraines and multiple sclerosis has not been realised before.

Reduction and Control of Diseases Such as that are Neuro-Inflammatory with Flumazenil and Naltrexone by Sustained Delivery Systems Both naltrexone and flumazenil help return the HPA axis (the interaction between the hypothalamus, pituitary gland, and adrenal glands, which plays an important role in the stress response) to normal in stressed animals in our studies. Neuro-inflammatory diseases, such as Alzheimer's, Parkinson's Disease and Multiple Sclerosis, are all increased by stress and we have found that naltrexone and flumazenil together decrease stress and inflammatory diseases. For this reason the combination of sustained release naltrexone and sustained release flumazenil using injections, implants or infusions would be expected to limit neuro-inflammatory diseases and their symptoms.

The Use of Sustained Release Naltrexone and Flumazenil in Control of Hypertension, Diabetes and Stress Related Diseases Stress causes elevation of Corticotrophin Releasing Factor (CRF) which we believe predisposes an individual to hypertension, as well as raising cortisol levels which increase the risk of diabetes. By delivering sustained release of flumazenil and naltrexone in populations predisposed to stress such, as indigenous populations, we have noted a reduction in insulin requirements, an improvement in Glucose Tolerance Test (GTT) results and a decrease in hypertension. This potential treatment for reducing these risks in populations has not been described before.

Reduction of Drug or Anxiety Induced Episodes of Psychosis by Flumazenil Alone or Flumazenil and Naltrexone in Combination We have noted that in patients with a history of psychosis following cassation of cannabis, amphetamines and alcohol that the use of flumazenil alone, or flumazenil and naltrexone, by sustained delivery methods prevents the onset of psychosis in those with a history of psychosis with each detoxification. This reduction in anxiety and paranoid symptoms as well as florid psychosis is so profound that there is a strong basis for using flumazenil in those presenting with extreme anxiety, paranoid thoughts, as well as psychosis from non-drug induced psychosis. We have therefore extended our treatment to help minimise psychotic symptoms in non-drug affected patients.

Reduction or Control of Depression Using Flumazenil and Naltrexone

We have noted that in those with severe depression that the DASS score reduces to the normal range gradually over a two week period after inserting naltrexone and flumazenil implants. This is the first description of depression being treated with sustained release flumazenil and naltrexone.

Reduction or Control of Anxiety, Depression or Psychosis Following Pregnancy or the Menopause Using Flumazenil Alone or Flumazenil and Naltrexone We have noted that the drop in progesterone that occurs just before mensuration, following delivery or following the menopause is a special time when naltrexone and flumazenil is useful in treating, depression, anxiety, psychotic symptoms or just paranoid thoughts in the population that we have been treating with sustained naltrexone and flumazenil.

Reduction or Control of Symptoms Associated with Parkinson's Disease Using Flumazenil Alone or Flumazenil and Naltrexone We have used naltrexone and flumazenil implants to reduce the symptoms associated with Parkinson's Disease in patients for up to a year. Our observations included a reduction in levodopa (L-dopa) doses to a quarter of the previous dose and increased mobility and a decrease in addiction symptoms.

Reduction of Ageing

Since our research has shown that both naltrexone and flumazenil reduce inflammatory disorders, it is anticipated that the use of flumazenil and naltrexone in accordance with the present invention will reduce symptoms and signs of ageing and may lead to longer lifetime survivals.

Reduction in Suicide Attempts for Poly-Drug Users During Detoxification

We have noted in our poly-drug using patients that suicide attempts are frequent with cannabis, alcohol and amphetamine withdrawal, and we have demonstrated a decrease in suicide attempts in our 12,000 poly-drug patients when we are treating these patients with sustained release naltrexone and flumazenil.

The invention claimed is:

1. A method of treating a patient suffering from a migraine and/or a headache, or multiple sclerosis comprising administering to the patient in need thereof an effective dose of flumazenil to achieve a blood concentration of flumazenil at about 0.5 ng/ml to 3.0 ng/ml flumazenil over a continuous period of time.

2. The method of claim 1, wherein the patient in need thereof is administered the effective dose of flumazenil of between 60 to 80 micrograms flumazenil per hour for the continuous period of time.

3. The method of claim 1 further comprising administering an effective dose of naltrexone.

4. The method according to claim 1, wherein the patient experiences premenstrual or postmenopausal symptoms associated with a decrease in progesterone; wherein the symptom is anxiety or psychosis.

5. The method of claim 1, wherein the patient is suffering from a migraine or multiple sclerosis, the method comprising the steps of: administering an initial subcutaneous infusion of flumazenil at a rate of 160 micrograms per hour, over a first continuous period of time to the subject; followed by administering a subcutaneous implant delivering about 60-80 micrograms per hour of flumazenil to obtain a blood level of about 0.5 ng/ml to 3.0 ng/ml flumazenil for a second continuous period of time.

6. The method of claim 1, wherein the patient is suffering from a migraine or multiple sclerosis, the method comprising the step of: administering a subcutaneous implant delivering about 60-80 micrograms per hour of flumazenil to obtain a blood level of about 0.5 ng/ml to 3.0 ng/ml flumazenil for a first continuous period of time.

7. The method according to claim 5 further comprising administering one or more additional subcutaneous implant delivering an estimated 60-80 micrograms per hour of flumazenil to obtain a blood level of about 0.5 ng/ml to 3.0 ng/ml flumazenil over one or more additional continuous periods of time.

8. The method according to claim 6 further comprising administering one or more additional subcutaneous implant delivering an estimated 60-80 micrograms per hour of flumazenil to obtain a blood level of about 0.5 ng/ml to 3.0 ng/ml flumazenil over one or more additional continuous periods of time.

9. The method of claim 5 further comprising administering a second subcutaneous implant delivering about 60-80 micrograms per hour of flumazenil to obtain a blood level of about 0.5 ng/ml to 3.0 ng/ml flumazenil over a third continuous period of time.

10. The method of claim 6 further comprising administering a second subcutaneous implant delivering about 60-80 micrograms per hour of flumazenil to obtain a blood level of about 0.5 ng/ml to 3.0 ng/ml flumazenil over a second continuous period of time.

* * * * *